US012797568B2

(12) United States Patent
Takatori et al.

(10) Patent No.: US 12,797,568 B2
(45) Date of Patent: Nov. 17, 2026

(54) AIRWAY ADAPTER

(71) Applicant: NIHON KOHDEN CORPORATION, Tokyo (JP)

(72) Inventors: Fumihiko Takatori, Tokorozawa (JP); Yuya Baba, Tokorozawa (JP); Kazumasa Ito, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 551 days.

(21) Appl. No.: 18/473,739

(22) Filed: Sep. 25, 2023

(65) Prior Publication Data

US 2024/0108837 A1 Apr. 4, 2024

(30) Foreign Application Priority Data

Oct. 3, 2022 (JP) ................................ 2022-159522

(51) Int. Cl.
*A61M 16/04* (2006.01)
*A61B 5/087* (2006.01)
*A61B 5/097* (2006.01)

(52) U.S. Cl.
CPC ......... *A61M 16/0404* (2014.02); *A61B 5/087* (2013.01); *A61B 5/097* (2013.01)

(58) Field of Classification Search
CPC .............. A61M 16/0404; A61M 16/04; A61M 16/0808; A61M 16/0833; A61M 16/0883; A61M 16/109; A61M 16/16; A61M 2016/0027; A61M 2016/0033; A61M 2016/102; A61M 2016/103; A61M 2205/3306; A61M 2209/084; A61M 2230/43; A61M 2230/432; A61M 16/0816; A61B 5/087; A61B 5/097
See application file for complete search history.

(56) References Cited

U.S. PATENT DOCUMENTS 5,279,578 A * 1/1994 Cooke ................. A61M 5/3213 604/263
5,720,282 A * 2/1998 Wright .................. A61M 16/04 128/207.14
5,722,959 A * 3/1998 Bierman ............... A61M 25/02 604/174
5,855,203 A 1/1999 Matter
(Continued)

FOREIGN PATENT DOCUMENTS

EP 2606820 A1 * 6/2013 ............. A61B 5/083
JP 2012-159386 A 8/2012
(Continued)

OTHER PUBLICATIONS

Japanese Office Action issued in Japanese Patent Application No. 2022-159522 dated Aug. 8, 2025.

*Primary Examiner* — Timothy A Stanis
*Assistant Examiner* — Matthew R Moon
(74) *Attorney, Agent, or Firm* — McDonald Hopkins LLC

(57) ABSTRACT

An airway adapter includes an airway adapter body including a first tube connection portion, a second tube connection portion, and a detection portion provided between the first tube connection portion and the second tube connection portion, and a support base configured to support the airway adapter body. The support base is configured to support the first tube connection portion at a position higher than a position of the second tube connection portion.

10 Claims, 12 Drawing Sheets

(56) References Cited

U.S. PATENT DOCUMENTS

| | | | | |
|---|---|---|---|---|
| 7,614,123 | B2 * | 11/2009 | Schweikert | A61M 39/105 24/522 |
| 8,585,655 | B2 * | 11/2013 | Bierman | A61M 25/02 604/174 |
| 2017/0086708 | A1 | 3/2017 | Takatori | |
| 2019/0105457 | A1 * | 4/2019 | Baba | A61M 16/085 |
| 2022/0257142 | A1 | 8/2022 | Takatori et al. | |
| 2022/0355059 | A1 | 11/2022 | Holyoake et al. | |

FOREIGN PATENT DOCUMENTS

| | | | | |
|---|---|---|---|---|
| JP | 2017-060554 A | | 3/2017 | |
| JP | 2022-124247 A | | 8/2022 | |
| JP | 2022-540415 A | | 9/2022 | |
| WO | WO-2021070720 A1 | * | 4/2021 | A61M 16/0003 |

* cited by examiner

AIRWAY ADAPTER

CROSS-REFERENCE TO RELATED APPLICATIONS

This application is based on and claims priority under 35 USC 119 from Japanese Patent Application No. 2022-159522 filed on Oct. 3, 2022, the entire content of which is incorporated herein by reference.

TECHNICAL FIELD

The presently disclosed subject matter relates to an airway adapter that is configured to pass respiratory air of a living body, and to which a sensor configured to detect a concentration of respiratory gas (carbon dioxide, oxygen, anesthesia gas, or the like) contained in the respiratory air of a living body can be attached.

BACKGROUND ART

In a case where respiration or oxygen inhalation is performed, an optical concentration detection can be used in order to measure a concentration of respiratory gas such as carbon dioxide contained in respiratory air of a subject such as a patient. An airway adapter disclosed in JP2012-159386A includes window portions that are sealed by transparent sealing members, on both sides of an air passage through which respiratory air passes. Then, a light emitting unit and a light receiving unit of a sensor are disposed outside the window portion, and a concentration of the carbon dioxide is detected based on absorption of infrared rays in the respiratory air inside the passage.

In an airway adapter disclosed in JP2017-060554A, a flow rate of the respiratory air is measured in addition to detection of the concentration of the carbon dioxide. In JP2017-060554A, an air passage is narrowed for measuring the flow rate, and measuring units are attached to pressure take-out portions provided on both sides of the air passage. The measurement unit includes a pressure sensor and configured to measure a flow rate based on a differential pressure.

Although inspired air during the respiration is heated and humidified, a temperature of the inspired air decreases and an amount of saturated water vapor decreases in a case where a respiration circuit is exposed to room temperature. Therefore, condensation occurring inside the respiration circuit accumulates inside the airway adapter. Further, a large amount of water vapor is also contained in expired air from a living body such as a subject, which causes condensation inside the respiration circuit. This also applies to oxygen inhalation or the like. In a case where the airway adapter is turned sideways, the window portion through which the infrared rays pass is located downward, and the window portion is covered with water.

In a case where an inside of the window portion for optical measurement is covered with water, the infrared rays are refracted by water and hardly enter the light receiving unit, and an optical path through which the respiratory air passes is shortened by an amount corresponding to a width covered with water. Further, in a case where water adheres to the pressure take-out portion or the like for pressure detection, an accurate pressure cannot be measured. In a case where the air passage is narrowed by water, an accurate flow rate may not be measured.

SUMMARY OF INVENTION

Aspect of non-limiting embodiments of the present disclosure relates to provide an airway adapter that is less likely to be affected by water generated due to condensation or the like, in a measurement of respiratory air using the airway adapter.

Aspects of certain non-limiting embodiments of the present disclosure address the features discussed above and/or other features not described above. However, aspects of the non-limiting embodiments are not required to address the above features, and aspects of the non-limiting embodiments of the present disclosure may not address features described above.

According to an aspect of the present disclosure, there is provided an airway adapter including:

- an airway adapter body including:
  - a first tube connection portion;
  - a second tube connection portion; and
  - a detection portion provided between the first tube connection portion and the second tube connection portion; and
- a support base configured to support the airway adapter body,
- in which the support base is configured to support the first tube connection portion at a position higher than a position of the second tube connection portion.

BRIEF DESCRIPTION OF DRAWINGS

Exemplary embodiment(s) of the present invention will be described in detail based on the following figures, wherein.

DESCRIPTION OF EMBODIMENTS

Figure 1:
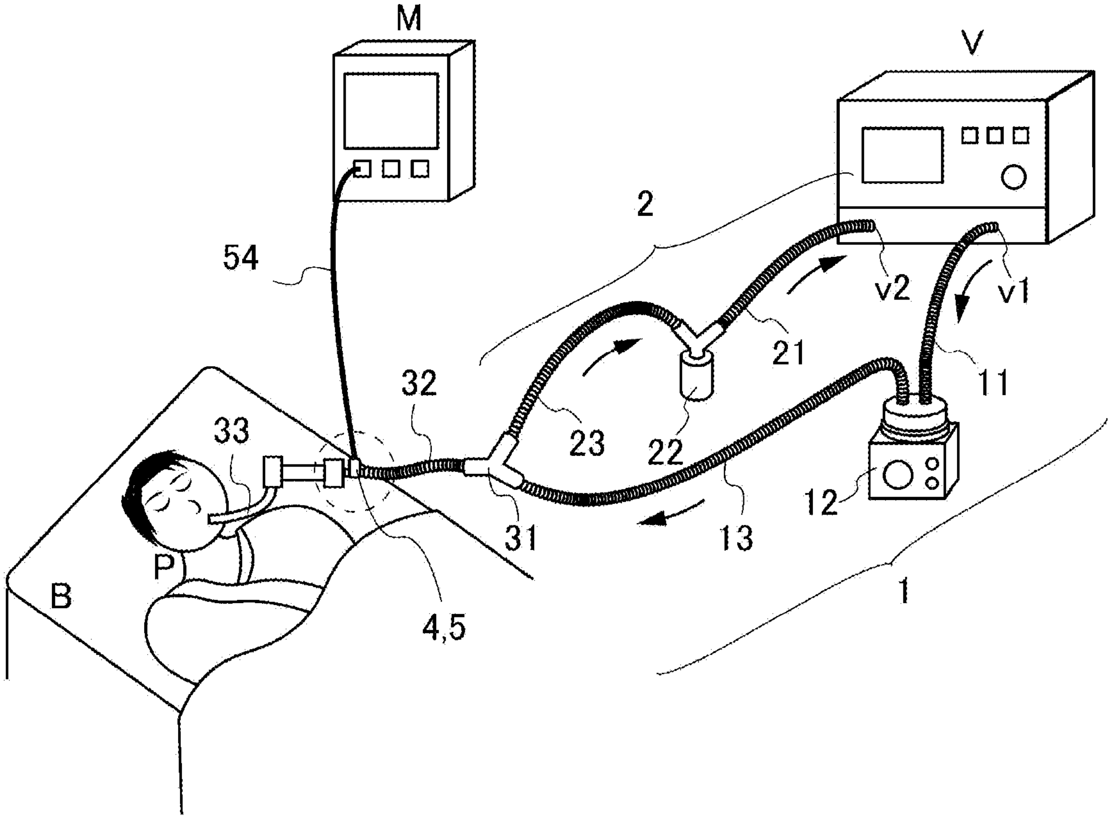
FIG. 1 illustrates a state of respiration using an airway adapter in the related art.

FIG. 1 schematically illustrates a related-art situation in which a respirator apparatus V is attached to a patient P lying on a bed B. In the respirator apparatus V, inspiration gas containing a large amount of oxygen is sent to the patient P, and expired air of the patient P is taken in. An inspiration circuit 1 is connected to an inspiration side connection portion v1 of the respirator apparatus V. An expiration circuit 2 is connected to an expiration side connection portion v2 of the respirator apparatus V. In the inspiration circuit 1, a corrugated tube 11 is connected to the inspiration side connection portion v1 of the respirator apparatus V, and a humidifier 12 is connected to the corrugated tube 11. Further, a corrugated tube 13 is connected to the humidifier 12, and the corrugated tube 13 is connected to a Y-piece 31. In the expiration circuit 2, a corrugated tube 21 is connected to the expiration side connection portion v2 of the respirator apparatus V, and a water trap 22 is connected to the corrugated tube 21. Further, a corrugated tube 23 is connected to the water trap 22, and the Y-piece 31 is connected to the corrugated tube 23. A flexible tube 32 is connected to a remaining connection portion of the Y-piece 31, and the flexible tube 32 is connected to an intubation tube 33 via an airway adapter 4 in the related art. The intubation tube 33 is inserted from a mouth to a trachea of the patient P.

Figure 2:
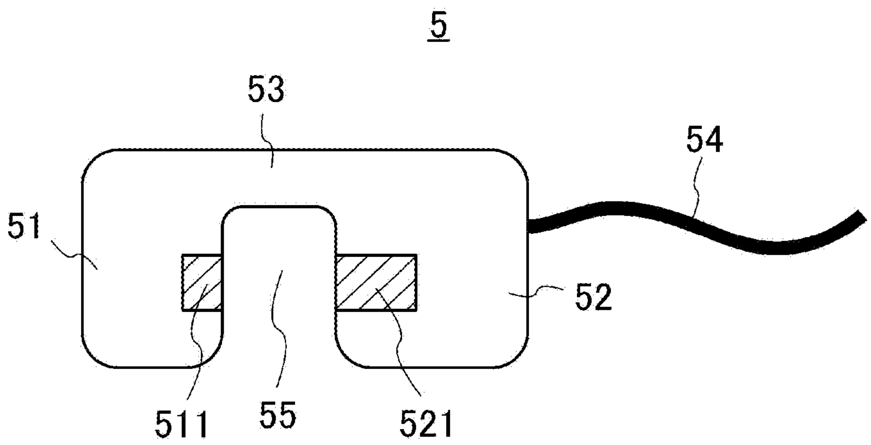
FIG. 2 illustrates a portion in a vicinity of an airway adapter in a respirator apparatus in the related art.

An optical sensor 5, which is a type of sensor, is attached to the airway adapter 4. The optical sensor 5 is configured to optically measure respiratory gas passing through an inside of the airway adapter 4. FIG. 2 illustrates the optical sensor 5. FIG. 2 illustrates the optical sensor 5 viewed from a direction of the flexible tube 32 in FIG. 1. The optical sensor 5 can include a first side portion 51, a second side portion 52, and a connection portion 53 that connects the first side portion 51 and the second side portion 52. A light receiving unit 511 is provided inside the first side portion 51. A light emitting unit 521 is provided inside the second side portion 52. The optical sensor 5 is attached to the airway adapter 4 such that the first side portion 51 and the second side portion 52 straddle the airway adapter 4.

In a case where the optical sensor 5 is attached to the airway adapter 4, the airway adapter 4 is located in a recess portion 55 illustrated in FIG. 2 and is clamped between the first side portion 51 and the second side portion 52. Then, infrared rays sent from the light emitting unit 521 pass through the inside of the airway adapter 4 and are received by the light receiving unit 511. A light reception value is sent to a patient monitor M via wiring 54 to calculate a concentration of the carbon dioxide, and the measured value is monitored.

Figure 3:
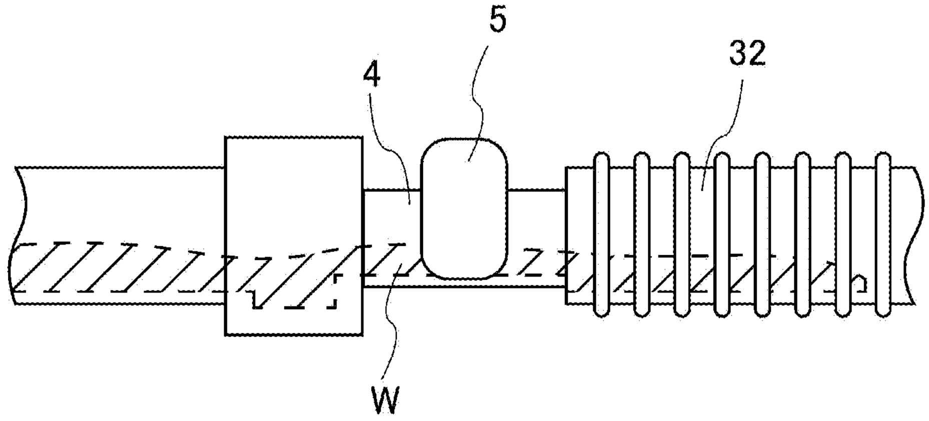
FIG. 3 illustrates a situation in which condensation occurs in a vicinity of an airway adapter and water accumulates.

As illustrated in FIG. 1, inspired air supplied from the respirator apparatus V is humidified by the humidifier 12. Further, expired air discharged from the patient P also contains water vapor. Therefore, condensation occurs inside the airway adapter 4 which is exposed to a temperature lower than a temperature of the humidifier or the expired air. FIG. 3 illustrates a situation in which condensation occurs inside the airway adapter 4 and water W accumulates. FIG. 3 is an enlarged view of a portion indicated by a dotted circle in FIG. 1. As illustrated in FIG. 3, the optical sensor 5 is attached to the airway adapter 4, and the optical sensor 5 is configured to optically measure respiratory gas. The optical sensor 5 is configured to irradiate, through a window of the airway adapter 4, the respiratory gas in the air passage with infrared rays to detect the infrared rays passing the window. The optical sensor 5 is configured to obtain an absorption rate of the infrared rays at a specific frequency to measure the concentration of carbon dioxide. However, in a case where the water W is present in the air passage that is a light path of the infrared rays as illustrated in FIG. 3, the infrared rays are absorbed by the water W and an underwater substance, or the infrared rays are refracted to change the light path. Then, a part of the infrared rays emitted from the light emitting unit 521 toward the light receiving unit 511 illustrated in FIG. 2 does not reach the light receiving unit 511. Further, in a case where the water W is partially present in the optical path of the infrared rays, a volume of the infrared rays absorbed by the respiratory gas decreases. Therefore, it is difficult to accurately measure the absorption rate of the infrared rays in the respiratory gas.

Embodiment 1

Figure 4:
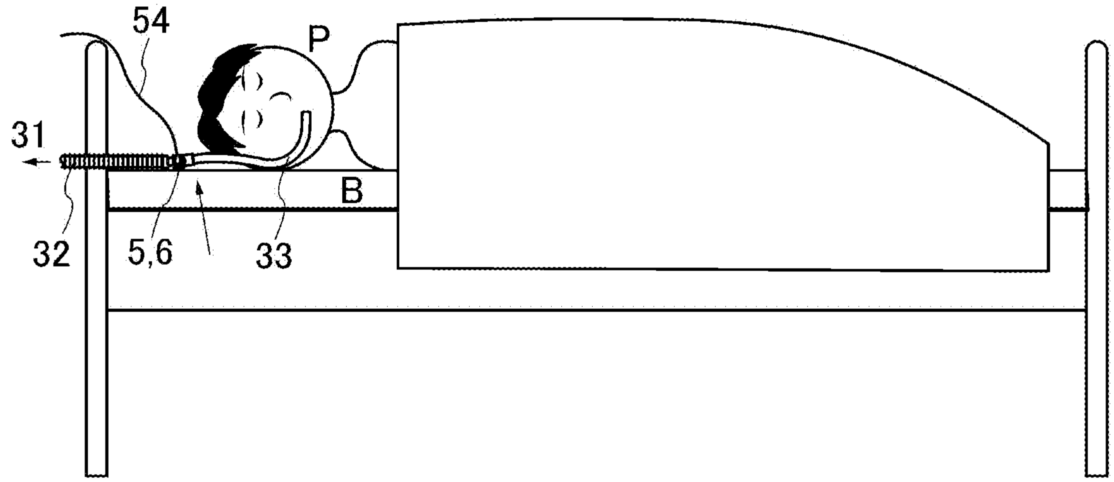
FIG. 4 illustrates a situation in which an airway adapter of Embodiment 1 is used in respiration of a respirator apparatus V.

FIG. 4 illustrates a situation in which an airway adapter 6 of Embodiment 1 is used for respiration in the respirator apparatus V. An intubation tube 33 is inserted into the mouth of the patient P. One end of the airway adapter 6 is connected to the intubation tube 33, and the other end is connected to the flexible tube 32. In FIG. 4, a configuration on a respirator apparatus V side of the Y-piece 31 and the patient monitor M are similar to those in FIG. 1 illustrating a state in the related art, and the description thereof is omitted. The flexible tube 32 of FIG. 4 is connected to the Y-piece 31. Further, the optical sensor 5 is attached to the airway adapter 6, and the optical sensor 5 is connected to the patient monitor M by the wiring 54 the same as or similarly to FIG. 1.

As indicated by an arrow in FIG. 4, the airway adapter 6 is placed on the bed B such that a patient P side is located high. Since an axis of the airway adapter 6 is slightly inclined, the condensed water W flows toward the flexible tube 32 and is discharged from the inside of the airway adapter 6. Therefore, the water W accumulated inside the airway adapter 6 is prevented from affecting the measurement.

Figure 5:
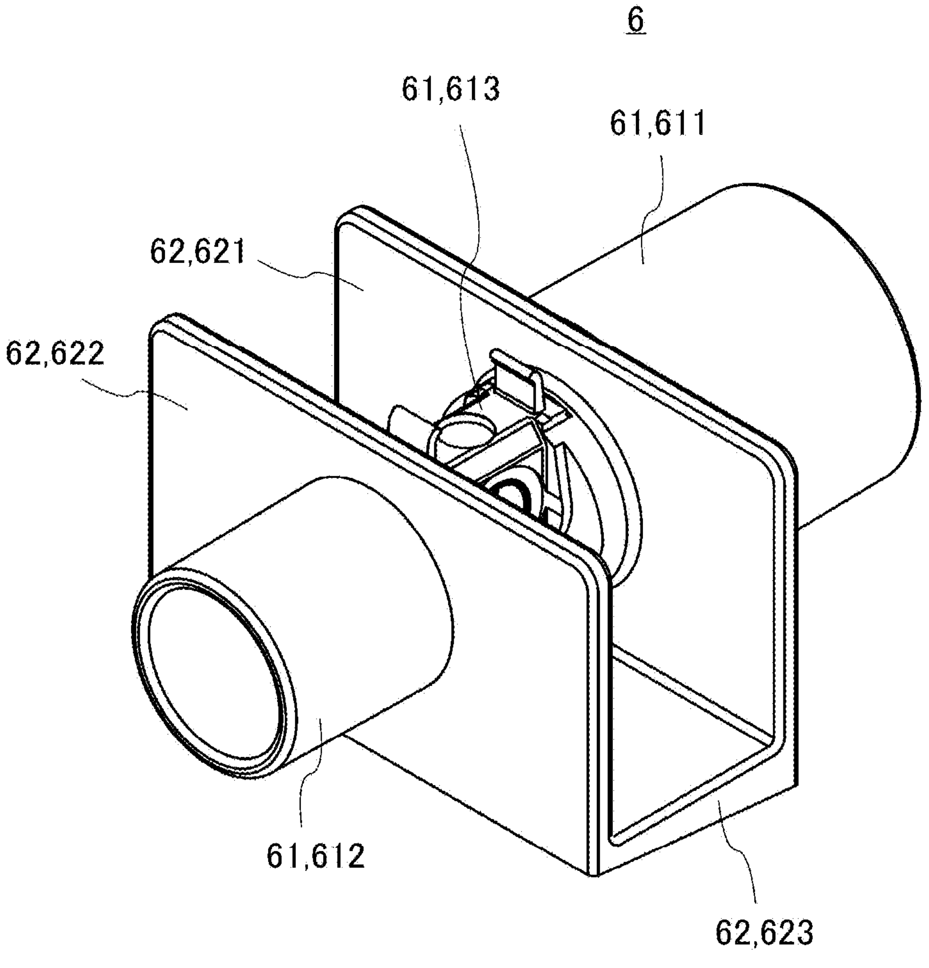
FIG. 5 is a perspective view of the airway adapter in Embodiment 1.

FIG. 5 is a perspective view of the airway adapter 6 according to Embodiment 1. The airway adapter 6 can include an airway adapter body 61 and a support base 62. The airway adapter body 61 and the support base 62 are integrated and are integrally formed of plastic. In the airway adapter body 61, a sensor attachment portion 613 that is a detection portion is provided between a first tube connection portion 611 and a second tube connection portion 612. Further, an attachment plate 621 and an attachment plate 622 are connected by a bottom plate 623 that is a bottom portion, to form the support base 62. Further, the attachment plate 621 is connected between the first tube connection portion 611 and the sensor attachment portion 613, the attachment plate 622 is connected between the second tube connection portion 612 and the sensor attachment portion 613, and the airway adapter body 61 is fixed to the support base 62.

Figure 6:
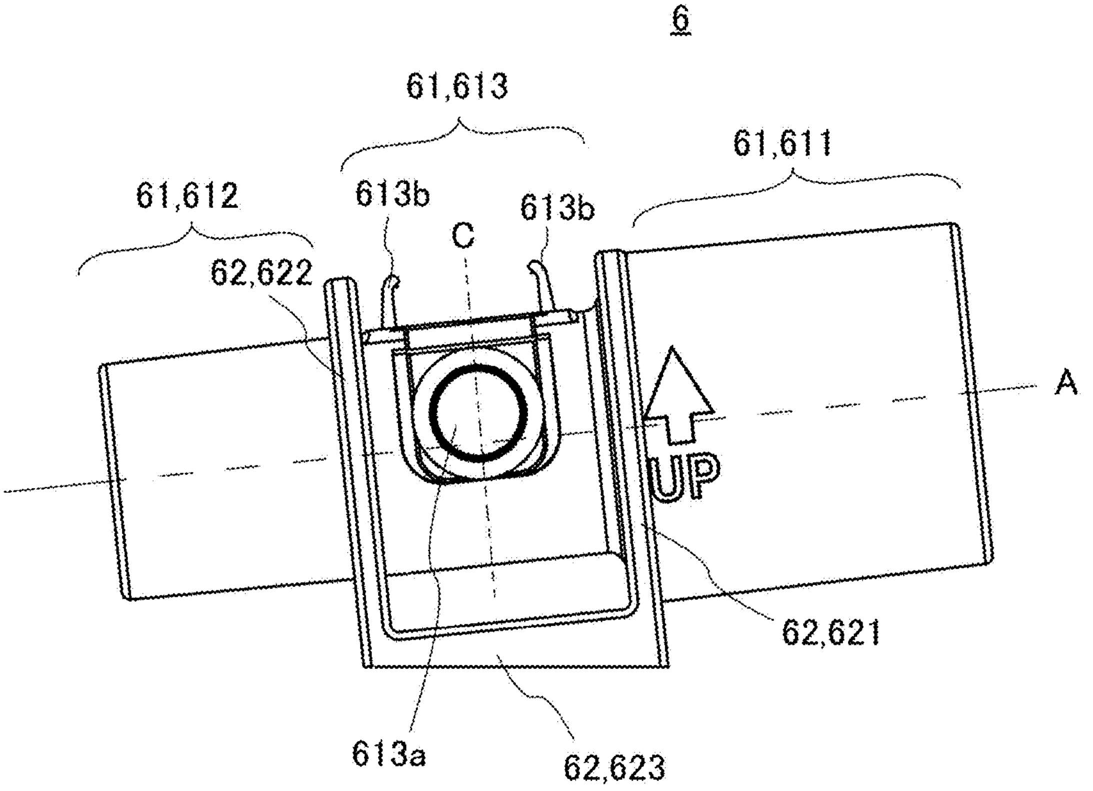
FIG. 6 is a side view of the airway adapter in Embodiment 1.

FIG. 6 is a side view of the airway adapter 6 according to Embodiment 1. The sensor attachment portion 613 is provided with window portions 613*a*. The window portions 613*a* are provided on both side surfaces of the airway adapter 6. Two locking protrusions 613*b* protrude above the sensor attachment portion 613.

Figure 7:
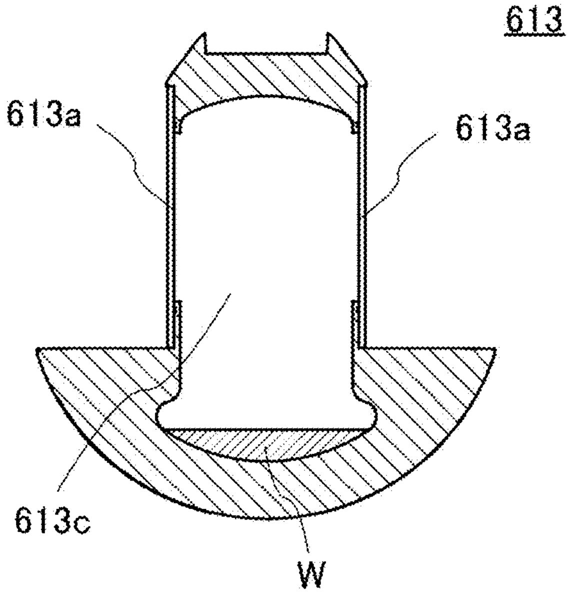
FIG. 7 is an enlarged view of a cross section of a sensor attachment portion in a portion indicated by an alternate long and short dash line C in FIG. 6.

FIG. 7 is an enlarged view of a cross section of the sensor attachment portion 613 in a portion indicated by an alternate long and short dash line C in FIG. 6. A substantially rectangular air passage 613*c* through which respiratory gas passes is formed inside the sensor attachment portion 613. The window portions 613*a* are formed on both sides of the air passage 613*c* and are sealed by transparent sealing members. The airway adapter 6 is integrally formed except for the sealing members.

Figure 8:
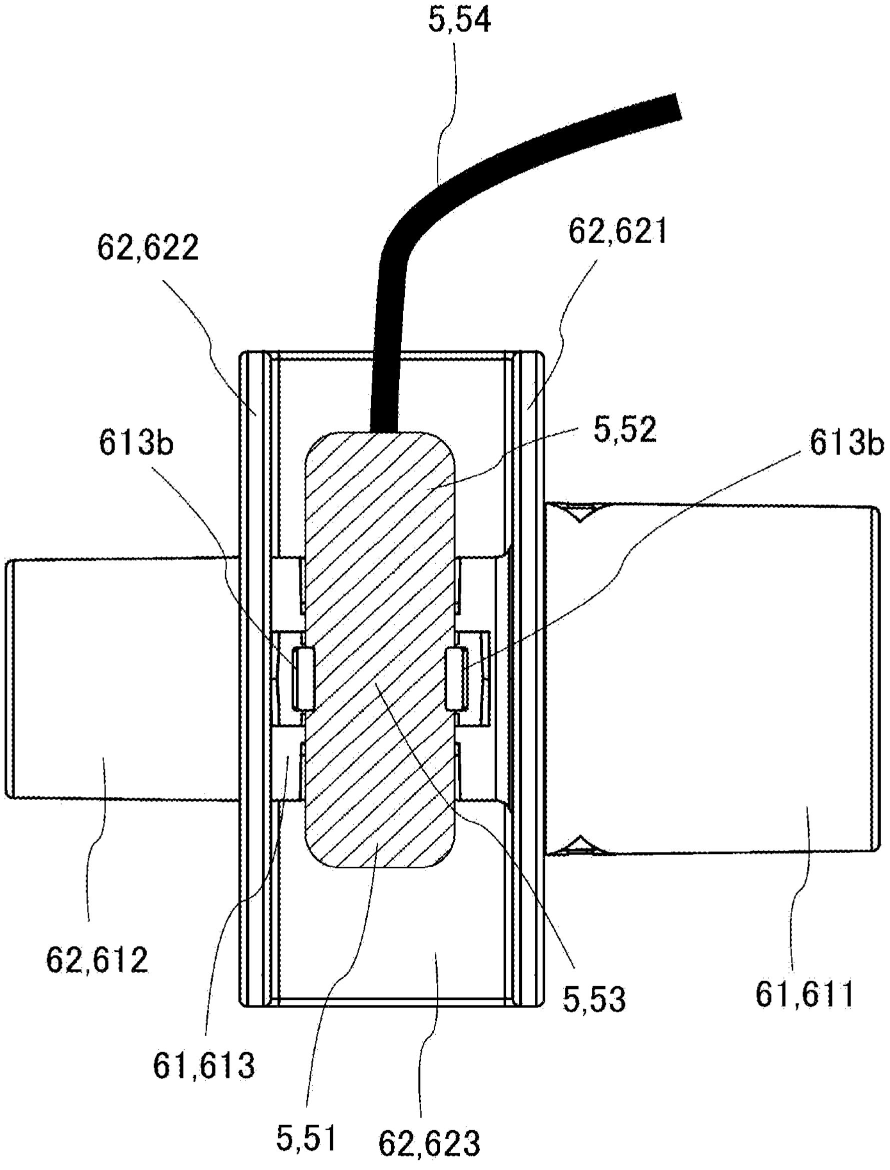
FIG. 8 is an oblique top view of the airway adapter to which an optical sensor in Embodiment 1 is attached.

FIG. 8 is an oblique top view of the airway adapter 6 to which the optical sensor 5 according to Embodiment 1 is attached. That is, FIG. 8 is a view that is viewed from an attachment direction of the optical sensor 5, and that is viewed from a slightly oblique direction from above. In the airway adapter body 61, a sensor attachment portion 613 that is a detection portion is provided between a first tube connection portion 611 and a second tube connection portion 612. The attachment plate 621 is connected between the first tube connection portion 611 and the sensor attachment portion 613. The attachment plate 622 is connected between the second tube connection portion 612 and the sensor attachment portion 613. The airway adapter body 61 is fixed to the support base 62.

As illustrated in FIG. 6, upper portions of the two locking protrusions 613*b* are bent inward. As illustrated in FIG. 8, the optical sensor 5 is locked such that a connection portion 53 is located inside the two locking protrusions 613*b*. A first side portion 51 and a second side portion 52 are provided on both sides of the connection portion 53.

In the airway adapter 6 according to Embodiment 1, the air passage 613*c* illustrated in FIG. 7 does not fall sideways due to the presence of the support base 62. Therefore, the window portions 613*a* are not covered with the water W, and the measurement of the optical sensor 5 is not affected.

Further, the water W generated due to condensation or the like flows out in a lower direction along an axis A of the airway adapter 6 due to gravity, at a lower portion of the air passage 613*c* illustrated in FIG. 7. Therefore, the water W does not stay in the air passage 613*c*. Therefore, the water W accumulated inside the airway adapter 6 is prevented from splashing in a case where the respiratory gas passes and is also prevented from affecting an optical path of the infrared rays. The water W flows to the flexible tube 32 through a lower portion of the air passage 613*c* and is discharged from the airway adapter 6.

As illustrated in FIG. 6, in the airway adapter 6 of Embodiment 1, a portion of the bottom plate 623, which is the bottom portion, close to the attachment plate 621 is formed thick and a bottom surface is inclined. The axis A, which is an axis of an inner hole passing through the airway adapter 6, is higher in the first tube connection portion 611. The first tube connection portion 611 is on the patient P side. Therefore, in a case where the airway adapter 6 is placed on the bed B as illustrated in FIG. 4, the axis A of the airway adapter 6 is higher on the patient P side, and the condensed water W flows into the flexible tube 32. Then, the water flows into the water trap 22 via the Y-piece 31 illustrated in FIG. 1.

In Embodiment 1, as illustrated in FIG. 8, a width of the bottom plate 623, which is the bottom portion of the support base 62, is larger than a width of the optical sensor 5, which is a sensor attached to the sensor attachment portion 613. Therefore, the airway adapter 6 is less likely to fall down in a width direction on the bed B or the like.

Embodiment 2

Figure 9:
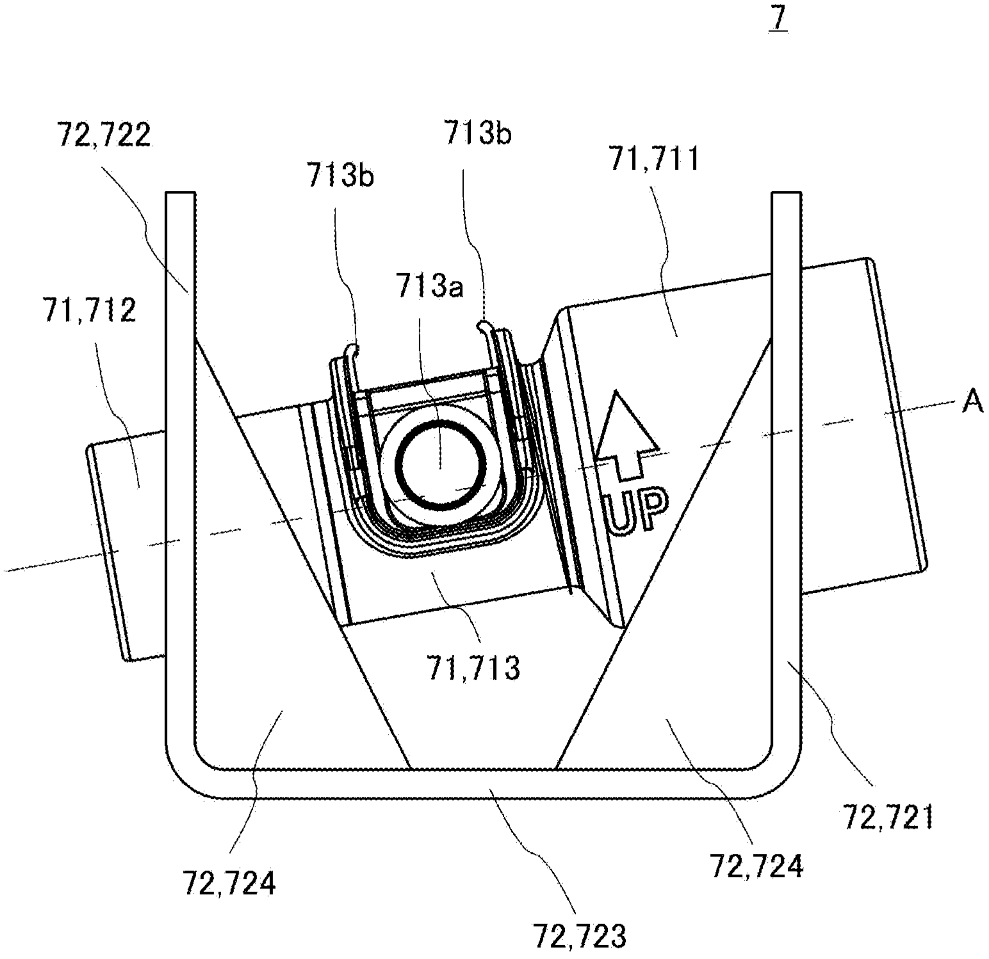
FIG. 9 is a side view of an airway adapter in Embodiment 2.

FIG. 9 is a side view of an airway adapter 7 according to Embodiment 2. The airway adapter 7 can include an airway adapter body 71 and a support base 72. The airway adapter body 71 and the support base 72 are formed separately, and are used in combination as illustrated in FIG. 8. In the airway adapter body 71, a sensor attachment portion 713, which is a detection portion, is provided between a first tube connection portion 711 and a second tube connection portion 712.

The sensor attachment portion 713 is provided with window portions 713*a*. The window portions 713*a* are provided on both side surfaces of the airway adapter body 71 and are sealed by transparent sealing members. Two locking protrusions 713*b* protrude above the sensor attachment portion 713. Upper portions of the two locking protrusions 713*b* are bent inward, and the optical sensor 5 is locked such that the optical sensor 5 is located inside the two locking protrusions 713*b*. These configurations are the same as those of Embodiment 1.

Figure 10:
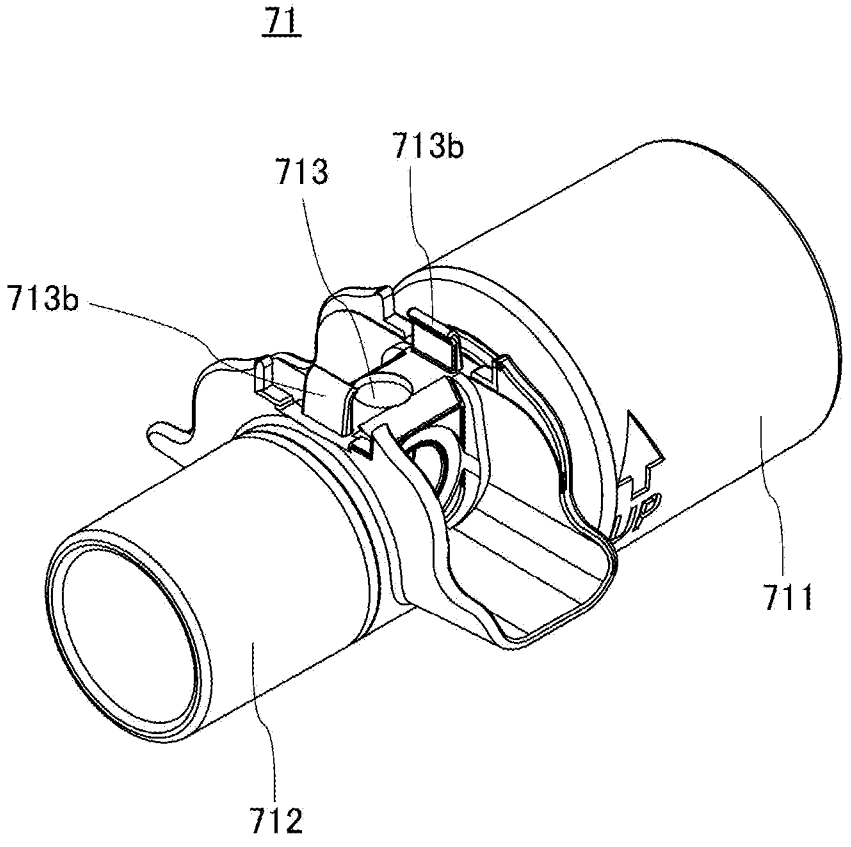
FIG. 10 is a perspective view of the airway adapter body in Embodiment 2.

FIG. 10 is a perspective view of the airway adapter body 71 with the support base 72 removed from the airway adapter 7. In the airway adapter body 71, a sensor attachment portion 713, which is a detection portion, is provided between a first tube connection portion 711 and a second tube connection portion 712. Further, locking protrusions 713*b* for locking the optical sensor 5 is provided above the sensor attachment portion 713.

Further, as illustrated in FIG. 9, the attachment plate 721 and the attachment plate 722 are connected by a bottom plate 723, which is a bottom portion, to form the support base 72. The attachment plate 721 and the bottom plate 723, and the attachment plate 722 and the bottom plate 723 are fixed by deformation prevention plates 724 each of which is a triangular plate. Four deformation prevention plates 724 are provided on both sides of the support base 72.

In the airway adapter 7, the first tube connection portion 711 is locked to the attachment plate 721, the second tube connection portion 712 is locked to the attachment plate 722, and the airway adapter body 71 is locked to the support base 72 such that the axis A is inclined. As illustrated in FIG. 9, the axis A is higher on a first tube connection portion 711 side than on a second tube connection portion 712 side.

Figure 11:
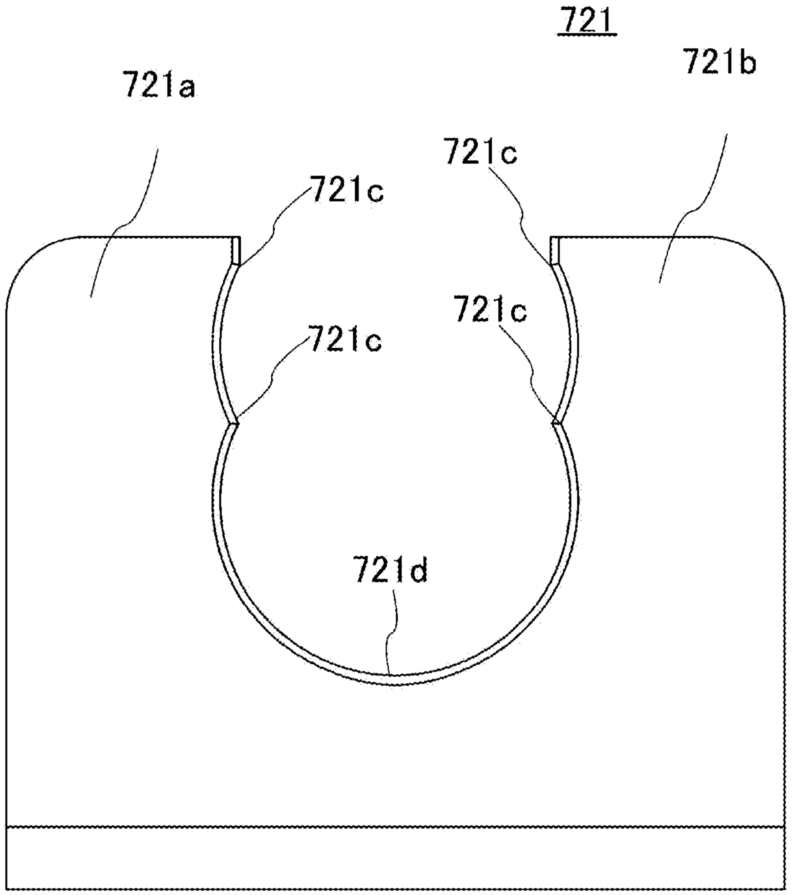
FIG. 11 is a front view of a support base in Embodiment 2.
Figure 12:
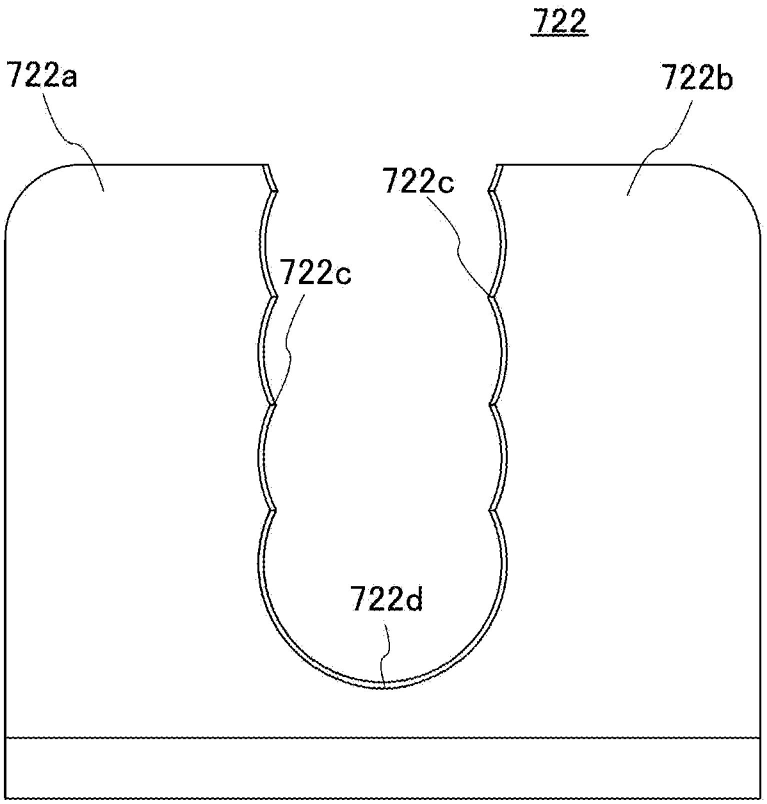
FIG. 12 is a rear view of the support base in Embodiment 2.

FIGS. 11 and 12 illustrate a front view and a rear view of the support base 72 according to Embodiment 2. FIG. 11 is a view of the support base 72 of FIG. 9 as seen from a right side, and FIG. 12 is a view of the support base 72 of FIG. 9 as seen from a left side. As illustrated in FIG. 11, the attachment plate 721 includes a first clamping portion 721*a* and a second clamping portion 721*b*. Each of the first clamping portion 721*a* and the second clamping portion 721*b* is provided with two locking protruding portions 721*c* in an upper-lower direction, and a lower support portion 721*d* is provided on a lower side. As illustrated in FIG. 12, the attachment plate 722 includes a first clamping portion 722*a* and a second clamping portion 722*b*. Each of the first clamping portion 722*a* and the second clamping portion 722*b* is provided with four locking protruding portions 722*c* in the upper-lower direction, and a lower support portion 722*d* is provided on the lower side. The lower support portion 721*d* is provided at a position higher than a position of the lower support portion 722*d*. A distance between the first clamping portion 721*a* and the second clamping portion 721*b* of the attachment plate 721 is larger than a distance between the first clamping portion 722*a* and the second clamping portion 722*b* of the attachment plate 722.

The first tube connection portion 711 of the airway adapter body 71 is configured to be clamped between the first clamping portion 721*a* and the second clamping portion 721*b* illustrated in FIG. 11. The locking protruding portions 721*c* and the lower support portion 721*d* is configured to press the first tube connection portion 711, to lock the first tube connection portion 711. Further, the second tube connection portion 712 is configured to be clamped between the first clamping portion 722*a* and the second clamping portion 722*b* illustrated in FIG. 12. The locking protruding portions 722*c* and the lower support portion 722*d* is configured to press the second tube connection portion 712, to lock the second tube connection portion 712.

Figure 13:
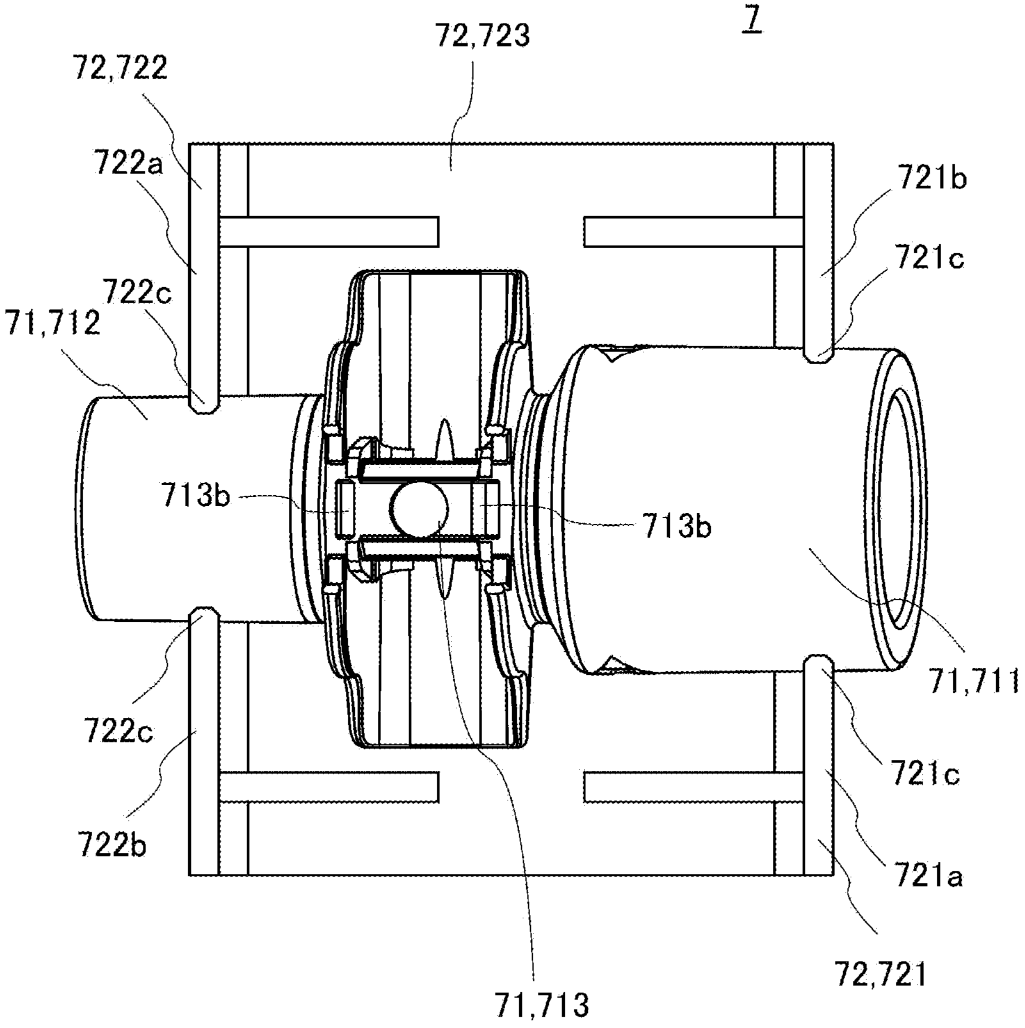
FIG. 13 is a top view of the airway adapter in Embodiment 2.

FIG. 13 is a top view of the airway adapter 7 according to Embodiment 2. As can be seen from FIGS. 10 to 13, the first tube connection portion 711 and the second tube connection portion 712 can be locked at a plurality of levels of height by the locking protruding portions 721*c* and the locking protruding portions 722*c*. By changing the locking height, inclination of the axis A of the airway adapter body 71 can be changed. The plastic forming the support base 72 has some elasticity, and in a case where the first tube connection portion 711 of the airway adapter body 71 is pushed between the first clamping portion 721*a* and the second clamping portion 721*b*, a space between the locking protruding portions 721*c* is temporarily expanded. Further, in a case where the second tube connection portion 712 is pushed between the first clamping portion 722*a* and the second clamping portion 722*b*, a space between the locking protruding portions 722*c* is temporarily expanded.

As illustrated in FIG. 13 and the like, an outer diameter of the first tube connection portion 711 is larger than an outer diameter of the second tube connection portion 712. The distance between the first clamping portion 721*a* and the second clamping portion 721*b* is set according to the first tube connection portion 711 having a larger outer diameter. The distance between the first clamping portion 722*a* and the second clamping portion 722*b* is set according to the second tube connection portion 712 having a smaller outer diameter. Although the airway adapter body 71 and the support base 72 of Embodiment 2 are formed separately, the airway adapter body 71 and the support base 72 are not combined in wrong directions due to a difference in outer diameter between the first tube connection portion 711 and the second tube connection portion 712.

Although not illustrated, in Embodiment 2, a width of the bottom plate 723, which is a bottom portion of the support base 72, is also larger than a width of the optical sensor 5, which is a sensor attached to the sensor attachment portion 713. Therefore, the airway adapter 7 is less likely to fall down in a width direction on the bed B or the like. Further, the bottom plate 723 of Embodiment 2 is also wide in a longitudinal direction which is a direction in which the axis A is projected onto the bottom plate 723. Therefore, in a case where the airway adapter 7 is placed on the bed B and a part of the bottom plate 723 is raised or lowered by the flexible tube 32 or the like, an angle of the axis A is less likely to be changed.

By changing the number of the locking protruding portions 721*c* and 722*c* in the attachment plates 721 and 722 of the support base 72, the number of positions at which the first tube connection portion 711 and the second tube connection portion 712 can be attached to the support base 72 can be changed. In Embodiment 2, the support base 72 is configured to change a height of at least one of a position in which the first tube connection portion 711 is attached to the support base 72 or a position in which the second tube connection portion 712 is attached to the support base 72. However, only one pair of locking protruding portions on one of the attachment plates 721 and 722 in the support base 72 may be provided, and the height of attachment position on the support base 72 can be changed for only one of the first tube connection portion 711 and the second tube connection portion 712.

Modification

Figure 14:
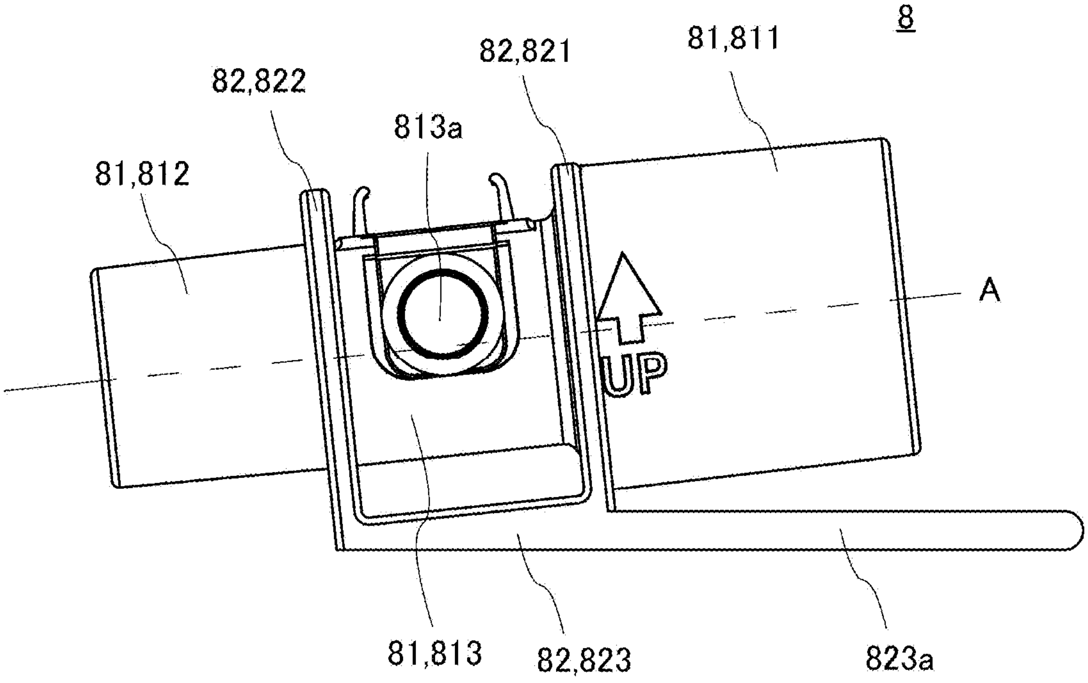
FIG. 14 is a side view of an airway adapter according to Modification 1.

FIG. 14 is a side view of an airway adapter 8 according to Modification 1, which is a modification of Embodiment 1. The airway adapter 8 can include an airway adapter body 81 and a support base 82. The airway adapter body 81 and the support base 82 are integrated and are integrally formed of plastic except for sealing members for window portions 813*a*. In the airway adapter body 81, a sensor attachment portion 813, which is a detection portion, is provided between the first tube connection portion 811 and the second tube connection portion 812. Further, an attachment plate 821 and an attachment plate 822 are connected by a bottom plate 823, which is a bottom portion, to form the support base 82. Further, the attachment plate 821 is connected between the first tube connection portion 811 and the sensor attachment portion 813. The attachment plate 822 is connected between the second tube connection portion 812 and the sensor attachment portion 813. The airway adapter body 81 is fixed to the support base 82. The optical sensor 5 is attached to the sensor attachment portion 813 to cover window portions 813*a*. These configurations are the same as those of Embodiment 1.

Further, in the airway adapter 8 of Modification 1, the same as or similarly to Embodiment 1, a portion of the bottom plate 823, which is the bottom portion below the sensor attachment portion 813, close to the attachment plate 821 is formed thick, and a bottom surface is inclined. As illustrated in FIG. 14, the axis A of the airway adapter 8 is higher on a first tube connection portion 811 side. The first tube connection portion 811 is on the patient P side. Therefore, in a case where the airway adapter 8 is placed on the bed B as illustrated in FIG. 4, the axis A of the airway adapter 8 is higher on the patient P side, and the condensed water W flows from the air passage (not illustrated) to the flexible tube 32 on a side far from the patient P. Then, the water flows into the water trap 22 via the Y-piece 31 illustrated in FIG. 1.

In Modification 1, unlike the airway adapter 6 of Embodiment 1, the bottom plate 823 can include a bottom plate extending portion 823*a*. The bottom plate extending portion 823*a* extends from a lower portion of the attachment plate 821 to a lower side of the first tube connection portion 811, and extends farther. A width of the bottom plate extending portion 823*a* is the same as that of the attachment plate 821. Due to the presence of the bottom plate extending portion 823*a*, in a case where the airway adapter 8 is placed on the bed B, the airway adapter 8 is less likely to roll laterally or a direction of the axis A is less likely to be raised or lowered by a force from the flexible tube 32 or the like, and further stabilization is achieved. It is also easy to attach the airway adapter 8 to the bed B by attaching a tape to a lower surface of the bottom plate extending portion 823*a*.

Figure 15:
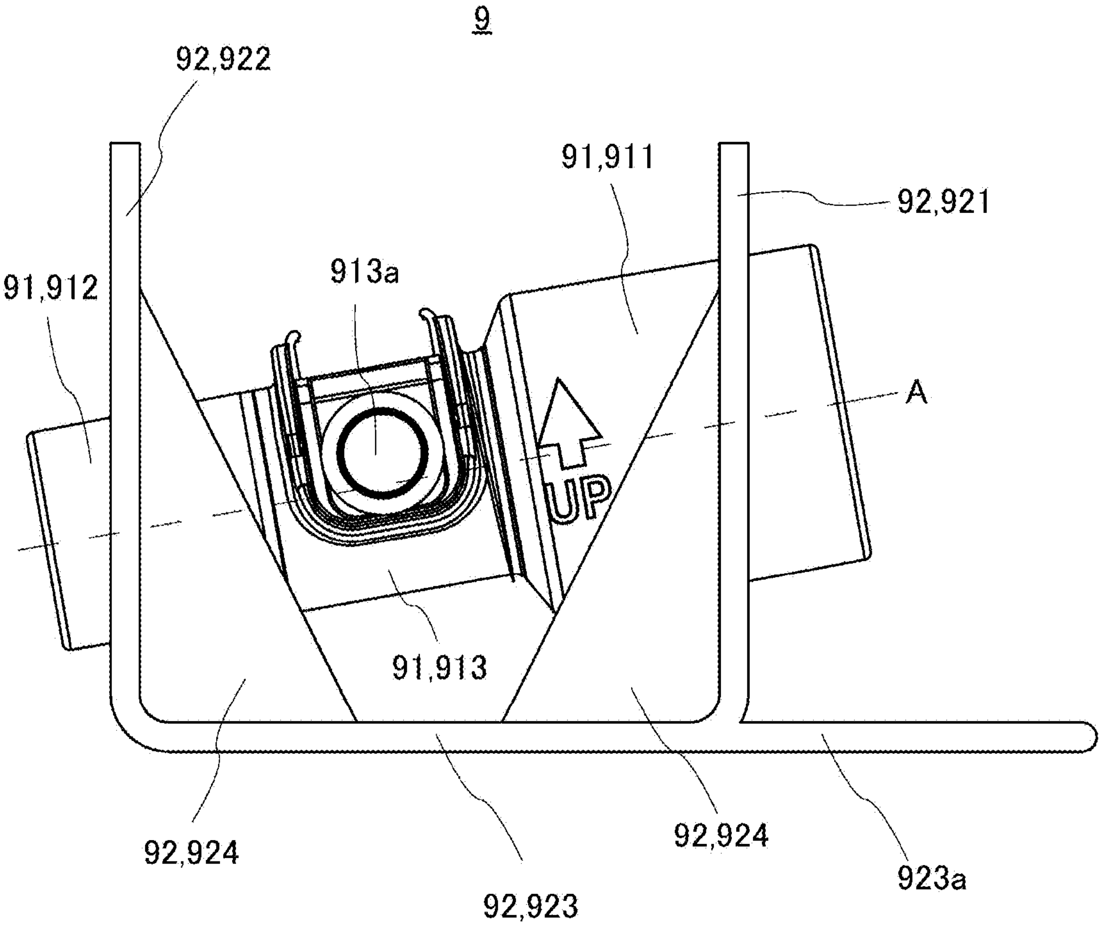
FIG. 15 is a side view of an airway adapter according to Modification 2.

FIG. 15 is a side view of an airway adapter 9 according to Modification 2, which is a modification of Embodiment 2. The airway adapter 9 can include an airway adapter body 91 and a support base 92. The airway adapter body 91 and the support base 92 are formed separately, and are used in combination as illustrated in FIG. 9. The airway adapter body 91 and the support base 92 are integrally formed of plastic. In the airway adapter body 91, a sensor attachment portion 913, which is a detection portion, is provided between a first tube connection portion 911 and a second tube connection portion 912. Further, an attachment plate 921 and an attachment plate 922 are connected by a bottom plate 923, which is a bottom portion, to form the support base 92. The attachment plate 921 and the bottom plate 923, and the attachment plate 922 and the bottom plate 923 are fixed by deformation prevention plates 924 each of which is a triangular plate. Four deformation prevention plates 924 are provided on both sides of the support base 92. Further, the attachment plate 921 is connected between the first tube connection portion 911 and the sensor attachment portion 913. The attachment plate 922 is connected between the second tube connection portion 912 and the sensor attachment portion 913. The airway adapter body 91 is fixed to the support base 92. The optical sensor 5 is attached to the sensor attachment portion 913 to cover window portions 913*a*. These configurations are the same as those of Embodiment 2.

In Modification 2, unlike the airway adapter 7 of Embodiment 2, the bottom plate 923, which is the bottom portion can include a bottom plate extending portion 923*a*. The rest is the same as in Embodiment 2. The bottom plate extending portion 923*a* extends from a lower portion of the attachment plate 921 to a lower side of the first tube connection portion 911, and extends farther. A width of the bottom plate extending portion 923*a* is the same as a width of the attachment plate 921. Due to the presence of the bottom plate extending portion 923*a*, in a case where the airway adapter 9 is placed on the bed B, a direction of the axis A is less likely to be raised or lowered by a force from the flexible tube 32 or the like, and further stabilization is achieved. It is also easy to attach the airway adapter 9 to the bed B by attaching a tape to a lower surface of the bottom plate extending portion 923*a*.

Further, although not illustrated, in Modification 3, one of the attachment plate 721 and the attachment plate 722 of Embodiment 2 may be fixed to the airway adapter body 71 as in Embodiment 1, and in the other of the attachment plate 721 and the attachment plate 722, a height of the locking protruding portion for locking the airway adapter body 71 may be changed as in Embodiment 2. In Modification 3, in order to facilitate change of an inclination angle of the attachment plate to which the airway adapter body 71 is fixed with respect to the bottom plate 723, it is preferable to set a lower portion of the attachment plate, a connection portion between the attachment plate and the bottom plate 723, and the like to be thin and to have a shape with high flexibility.

As Modification 4, in the airway adapter bodies of Embodiments 1 and 2, the first tube connection portion and the second tube connection portion may be connected to the sensor attachment portion to be rotatable around the axis A, which is a central axis of the airway adapter body. The sensor attachment portion, which is the detection portion, is configured to rotate with respect to the first tube connection portion and the second tube connection portion, and it is easy to finely adjust an angle of the sensor attachment portion in order to easily discharge the water in the airway adapter body in a lower direction.

The embodiments and the modifications described above can also be applied to an airway adapter for measuring a flow rate which can include a pressure take-out portion for pressure detection as in JP2017-060554A. A vicinity of the pressure take-out portion forms the detection portion. Since the water W does not stay in the vicinity of the pressure take-out portion, which is the detection portion, an accurate pressure can be detected and an accurate flow rate can be measured. The configuration can be used not only for the measurement of the concentration of carbon dioxide and the flow rate, but also for other measurements affected by the water W generated due to condensation or the like. Further, although an embodiment of a method of directly measuring the expired air, which is a main stream method, is described in the embodiment as a measurement for the expired air, a measurement method of sucking a part of the expired air, which is a side stream method, may be used.

In the above detailed description of the presently disclosed subject matter, it is assumed that the airway adapter is used for a patient. However, the airway adapter may be used for a subject other than a patient.

In addition, the specific configurations are not limited to the embodiments and the modifications, and changes and the like of the design without departing from the gist of the presently disclosed subject matter are also included in the presently disclosed subject matter. In addition, as long as there is no particular contradiction or problem in the purpose, configuration or the like of the above embodiments and modifications, techniques of the above embodiments and modifications can be used and combined.

What is claimed is:

1. An airway adapter comprising:

an airway adapter body including:

a first tube connection portion;

a second tube connection portion; and a detection portion provided between the first tube connection portion and the second tube connection portion; and a support base configured to support the airway adapter body, wherein the support base is configured to support the first tube connection portion at a position higher than a position of the second tube connection portion, wherein the support base comprises a bottom portion having a flat bottom surface and an inclined top surface opposite the bottom surface, a first attachment plate configured to support the first tube connection portion, and a second attachment plate configured to support the second tube connection portion, and wherein each of the first attachment plate and the second attachment plate protrudes from the inclined top surface of the bottom portion.

2. The airway adapter according to claim 1, wherein the detection portion is a sensor attachment portion.

3. The airway adapter according to claim 2, wherein a width of the bottom portion of the support base is larger than a width of a sensor attached to the sensor attachment portion.

4. The airway adapter according to claim 1, wherein the airway adapter body and the support base are formed integrally.

5. The airway adapter according to claim 1, wherein the airway adapter body and the support base are formed separately.

6. The airway adapter according to claim 5, wherein, the detection portion of the airway adapter body is configured to rotate with respect to the first tube connection portion and the second tube connection portion.

7. The airway adapter according to claim 5, wherein the first tube connection portion and the second tube connection portion is configured to be attached to the support base to attach the airway adapter body to the support base.

8. The airway adapter according to claim 7, wherein the support base is configured to change a height of at least one of a position in which the first tube connection portion is attached to the support base or a position in which the second tube connection portion is attached to the support base.

9. The airway adapter according to claim 8, wherein the first attachment plate or the second attachment plate includes a first clamping portion and a second clamping portion, the first clamping portion and the second clamping portion being configured to clamp the first tube connection portion or the second tube connection portion, at least one of the first clamping portion or the second clamping portion includes a locking protruding portion, in a case where the first clamping portion includes the locking protruding portion, the locking protruding portion included in the first clamping portion protrudes in a direction toward the second clamping portion, and in a case where the second clamping portion includes the locking protruding portion, the locking protruding portion included in the second clamping portion protrudes in a direction toward the first clamping portion.

10. The airway adapter according to claim 9, wherein an outer diameter of one of the first tube connection portion and the second tube connection portion is larger than an outer diameter of an other of the first tube connection portion and the second tube connection portion.

* * * * *